US00RE43979E

(19) United States
(12) Reissued Patent
Fodstad et al.

(10) Patent Number: US RE43,979 E
(45) Date of Reissued Patent: Feb. 5, 2013

(54) METHOD FOR DETECTION OF SPECIFIC TARGET CELLS IN SPECIALIZED OR MIXED CELL POPULATION AND SOLUTIONS CONTAINING MIXED CELL POPULATIONS

(75) Inventors: Oystein Fodstad, Oslo (NO); Gunnar Kvalheim, Oslo (NO)

(73) Assignee: Abbott Laboratories, Abbott Park, IL (US)

(21) Appl. No.: 10/359,677

(22) Filed: Feb. 5, 2003

Related U.S. Patent Documents

Reissue of:
(64) Patent No.: 6,184,043
Issued: Feb. 6, 2001
Appl. No.: 08/881,393
Filed: Jun. 24, 1997

U.S. Applications:
(62) Division of application No. 08/403,844, filed as application No. PCT/NO93/00136 on Sep. 10, 1993, now Pat. No. 6,893,881.

(30) Foreign Application Priority Data

Sep. 14, 1992 (WO) ..... PCT/NO92/00151

(51) Int. Cl.
*G01N 33/553* (2006.01)

(52) U.S. Cl. ..... 436/526; 435/7.1; 435/7.2; 435/7.23; 435/7.24; 435/7.25; 435/7.5; 435/7.8; 435/7.94; 435/40.5; 435/174; 435/181; 435/961; 435/2; 435/40; 435/52; 436/513; 436/518; 436/523; 436/532; 436/534; 436/538; 436/540; 436/824; 436/828

(58) Field of Classification Search ..... 435/7.1, 435/7.2, 7.23, 7.24, 7.25, 7.5, 7.8, 7.94, 40.52, 435/174, 181, 961; 436/513, 518, 523, 526, 436/532, 534, 538, 540, 824, 828
See application file for complete search history.

(56) References Cited

U.S. PATENT DOCUMENTS

| | | | |
|---|---|---|---|
| 4,219,411 | A | 8/1980 | Yen et al. |
| 4,497,900 | A | 2/1985 | Abram et al. |
| 4,510,244 | A | 4/1985 | Parks et al. |
| 4,511,662 | A | 4/1985 | Baran et al. |
| 4,659,678 | A | 4/1987 | Forrest et al. |
| 4,710,472 | A | 12/1987 | Saur et al. |
| 4,752,569 | A | 6/1988 | Terasaki et al. |
| 4,847,199 | A | 7/1989 | Snyder et al. |
| 4,857,452 | A | 8/1989 | Ho |
| 4,920,061 | A | 4/1990 | Poynton et al. |
| 4,925,922 | A | 5/1990 | Byers et al. |
| 5,019,497 | A | 5/1991 | Olsson |
| 5,095,097 | A | 3/1992 | Hermentin et al. |
| 5,194,300 | A | 3/1993 | Cheung |
| 5,219,763 | A | 6/1993 | Van Hoegaerden |
| 5,256,532 | A | 10/1993 | Melnicoff et al. |
| 5,264,344 | A | 11/1993 | Sneath |
| 5,290,707 | A | 3/1994 | Wood |
| 5,322,678 | A | 6/1994 | Morgan, Jr. et al. |
| 5,326,696 | A | 7/1994 | Chang |
| 5,340,719 | A | 8/1994 | Hajek et al. |
| 5,374,531 | A | 12/1994 | Jensen |
| 5,385,822 | A | 1/1995 | Melnicoff et al. |
| 5,405,784 | A | 4/1995 | Van Hoegaerden |
| 5,422,277 | A | 6/1995 | Connelly et al. |
| 5,424,213 | A | 6/1995 | Mougin |
| 5,491,068 | A | 2/1996 | Benjamin et al. |
| 5,514,340 | A | 5/1996 | Lansdorp et al. |
| 5,536,644 | A | 7/1996 | Ullman et al. |
| 5,624,815 | A | 4/1997 | Grant et al. |

FOREIGN PATENT DOCUMENTS

| | | | |
|---|---|---|---|
| DE | 3811566 | | 10/1988 |
| EP | 0 016 552 | | 10/1980 |
| EP | 0016552 | | 10/1980 |
| EP | 098 534 | | 1/1984 |
| EP | 131 934 | | 1/1985 |
| EP | 241 042 | | 10/1987 |
| EP | 256 471 | | 2/1988 |
| EP | 129 434 | | 9/1989 |
| EP | 339 769 | | 11/1989 |
| EP | 403960 | | 6/1990 |
| EP | 0395355 | | 10/1990 |
| EP | 0403960 | | 12/1990 |
| EP | 537 827 | | 4/1993 |
| EP | 0749580 | A1 | 12/1996 |
| FR | 2638849 | | 5/1990 |
| WO | WO 88/05309 | | 7/1988 |
| WO | 90/73800 | | 7/1990 |
| WO | 90/10692 | | 9/1990 |
| WO | 91/01368 | | 2/1991 |
| WO | WO 91/09058 | | 6/1991 |
| WO | 91/09938 | | 7/1991 |
| WO | 91/15766 | | 10/1991 |
| WO | 92/04961 | | 4/1992 |

(Continued)

OTHER PUBLICATIONS

Bosnes et al., Journal of Neurosurgery, 1989, 71:218.
Dynal Technical Documents, "Immunomagnetic Separations Using Dynabeads®," 1989.
Ho et al., Medical Laboratory Science, 1989, 46:324.
Hovdeness et al., Second. Journal Immunol., 1989, 26:631.

(Continued)

*Primary Examiner* — Christopher L Chin
(74) *Attorney, Agent, or Firm* — Lisa V. Mueller; Michael Best & Friedrich LLP

(57) ABSTRACT

The invention relates to a method for detecting specific target-cells in a simple and time saving way, using paramagnetic particles, antibodies recognizing the Fc portions of target-cell associating antibodies and target-cell associating antibodies directed to specific antigen determinants in the target-cell membranes. Incubation of the cell suspension with a mild detergent and/or second set of antibodies or antibody fragments, prelabeled or not with fluorescent agents, metallocolloids, radioisotopes, biotincomplexes or certain enzymes allowing visualization, with dramatically increase the specificity of the method. The method can further be used for isolation of the target-cells by magnetic field application and kit for performing the method according to the invention is described.

41 Claims, No Drawings

FOREIGN PATENT DOCUMENTS

| | | |
|---|---|---|
| WO | WO 94/02016 | 2/1994 |
| WO | 94/07138 | 3/1994 |
| WO | WO 94/07139 | 3/1994 |
| WO | WO 94/07142 | 3/1994 |
| WO | 95/24648 | 9/1995 |
| WO | WO 95/34817 | 12/1995 |
| WO | WO 96/31777 | 10/1996 |

OTHER PUBLICATIONS

Leven et al., British Journal of Haematology, 1989, 77:267.
Rana et al., Journal of Immunological Methods, 1989, 115:209.
Dynal Technical Document, "Dynabeads® M-450 CD4 (T-helper/indeucer cells)," 1990.
Dynal Technical Handbook, "General Cell Separation," 1992.
George et al., Thrombosis and Haemostasis, 1992, vol. 67:147.
Kemmer et al., Journal of Immunological Methods, 1992, 147:197.
Kvale et al., International Journal of Cancer, 1992, 42:638.
Hebell, T. And O. Gotze. 1989. The isolation of B lymphocytes from human peripheral blood using antibodies coupled to paramagnetic particles and rosetting techniques. J. Immunol. Meth. 123:283-291.
C.I. Civin, et al., "Positive stem cell selection—basic science", Progress in Clinical and Biological Research, vol. 333, 1990, pp. 387-402.
D. Pilling, et al., "The kinetics of interaction between lymphocytes and magnetic polymer particles", National Library of Medicine, File Medline, Medline accession No. 90010165, Sep. 1, 1989, 122(2) pp. 235-241.
E. H. Dunlop, et al., "Magnetic separation in biotechnology", Biotech ADVS, vol. 2, 1984, pp. 66-69.
C.H Setchell, "Magnetic Separations in Biotechnology—a Review", J. Chem. Tech. Biotechnol, vol. 35B, No. 3, 1985, pp. 175-182.
J.H. Pizzonia, et al., "Immunomagnetic seperation, primary culture, and characterization of cortical thick ascending limb plus distal convoluted tubule cells from mouse kidney", National Library of Medicine, File Medline, Medline accession No. 07783249, In Vitro Cell Dev Biol May 1991, 27A (5), pp. 409-416.
R.M. Leven, et al., "Immunomagnetic bead isolation of megakaryocytes from guinea-pig bone marrow: effect of recombinant interleukin-6 on size, ploidy and cytoplasmic fragmentation", National Library of Medicine, File Medline, Medline accession No. 07671620, Br J Haematol Mar. 1991, 77 (3), pp. 267-273.
G. Kvalheim, et al., "Elimination of B-Lymphoma Cells from Human Bone Marrow: Model Experiments Using Monodisperse Magnetic Particles Coated with Primary Monoclonal Antibodies", Cancer Research, vol. 47, Feb. 1987, pp. 846-851.
J.T. Kemshead, et al., "Monoclonal antibodies and magnetic microspheres for the depletion of leukaemic cells from bone marrow harvested for autologous transplantation", Bone Marrow Transplantation, vol. 2, 1987, pp. 133-139.
G. Kvalheim, et al., "Immunomagnetic purging of B-lymphoma cells from human bone marrow", Dialog Information Services, File 159, Cancerlit., Dialog accession No. 00559663, Fourth European Conference on Clinical Oncology and Cancer Nursing, Nov. 1-4, 1987, Madrid, Federation of European Cancer Societies, pp. 262, 1987.
T. Lea, et al, "Monosized, magnetic polymer particles: their use in separation of cells and subcellular components, and in the study of lymphocyte function in vitro", National Library of Medicine, File Medline, Medline accession No. 90234499, J Mol Recognit Feb. 1988; 1(1): 9-18.
Bio/Technology, vol. 11, Bjorn-Ivar Haukanes et al., "Application of Magnetic Beads in Bioassays" p. 60, Jan. 1993.
Scand J. Immunol, vol. 31, J. Heldrup, "A New Technique Using an Aggregating Antibody Against Glycophorin in-A for Puring Ficoll-Paque-Separated Leucocytes of Contaminating Erythroid Lineage Cells", pp. 289-296, see "Materials and methods" and p. 295, right column, 1990.
Rye, et al.; "Immunobead Filtration"; American Journal of Pathology, Jan. 1997; vol. 150, No. 1, pp. 99-107.
A. Bennick et al.; "A Rapid Method for Selecting Specific Hybridoma Clones using Paramagnetic Dynabeads"; Scand. J. Immunol.; 1993; pp. 212-214.
Abstract of Accession No. 90658782 Cancerlit; "Fourth International Conference on Monoclonal Antibody Immunoconjugates for Cancer"; Mar. 30-Apr. 1, 1989, San Diego, CA, UCSD Cancer Center.
Abstract of Crews J.R. et al.; Int. Journ. of Cancer; Jul. 9, 1992; vol. 51, No. 2.
Dialog Information Service, File 159, Cancerlit, Dialog accession No. 01046200, Cancerlit accession No. 94290389, Lemoli RM et al: "Positive selection of hematopietic CD34+ stem cells provides 'indirect purging' of CD34- lymphoid cells and the purging efficiency is increased by anti-CD2 and anti-CD30 immunotoxins", Bone Marrow Transplant; 13(4):465-71, 1994.
Dialog Information Service, File 159, Cancerlit, Dialog accession No. 01018250, Cancerlit accession No. 94084695, Myklebust AT et al: "Comparision of two antibody-based methods for elimination of breast cancer cells from hman bone marrow", Cancer Res; 54(1):209-14, 1994.
Dialog Information Service, File 159, Cancerlit, Dialog accession No. 00803246, Cancerlit accession No. 91348943, Tecce R. et al: "Production and Characterization of two Immunotoxins Specific for M5B An11 Leukaemia", Int J Cancer 49(2):310-6, 1991.
Dialog Information Service, File 159, Cancerlit, Dialog accession No. 00447849, Cancerlit accession No. 86110672, Tonevitsky AG et al: "Elimination of Murine Erythroleukemic Stem Cells with a Novel Anti-Erythroid Antibody Conjugated to Ricin a-chain: A Model for Studies of Bone-Marrow Transplantation Therapy", Int. J. Cancer; 37(2):263-73, 1986.
Dialog Information Service, File 159, Cancerlit, Dialog accession No. 01268628, Cancerlit accession No. 97031812, Kvalheim G. et al: "Purging of tumor cells from leukapheresis products: experimental and clinical aspects", J. Hematother; 5(4):427-36, 1996.
K.M. Stray, et al.; "Purging Tumor Cells from Bone Marrow or Peripheral Blood Using Avidin-Biotin Immunoadsorption"; Advances in Bone Marrow Purging and Processing; 1994; Orlando: Wiley-Liss, Inc.; pp. 97-103.
Hitoshi Maeda; "Applicability of an Immuno-microsphere Technique for a Forensic Identification of ABO Blood Types: The Use of Fluorescent Microspheres"; Jpn J. Legal Med.; 1989; pp. 322-327.
Andrew J. Beavis, et al.; "Detection of Cell-Surface Antigens Using Antibody-Conjugated Fluorosphers (ACF): Application for Six-Color Immunofluorescence"; Biotechniques; 1996; pp. 498-503.
Derwent acession No. 93-173192, Toyobo KK: "Sensitivity detection of ligand-receptor reaction-by combining fluorescent fine particles with objective substance, passing mixt. through flow cytometer, counting number of agglomerates etc."; & JP,A,5107249, 930427, DW9321.
K.A. Muirhead, et al.; "Flow Cytometry: Present and Future"; Biotechnology; Apr. 1985; vol. 3, pp. 337-356.
Michael J. Bjorn, et al.; "Antibody-Pseudomonas Exotoxin A Conjugates Cytotoxic to Human Breast Cancer Cells in Vitro"; Cancer Research; Jul. 1986; pp. 3262-3267.
Ian C. Anderson, et al.; "Elimination of Malignant Clonogenic Breast Cancer Cells from Human Bone Marrow"; Cancer Research; pp. 4659-4664, 1989.
K.C. O-Briant, MS, et al.; Elimination of Clongenic Breast Cancer Cells from Human Bone Marrow; Cancer; 1991; pp. 1272-1278.
C.L. Tyer, et al.; "Breast Cancer Cells are Effectively Purged from Peripheral Blood Progenitor cells Using an Immunomagnetic Technique"; Abstract to First Meeting of International Society for Hematotherapy and Graft Engineering, Orlando, Fl, 1993.
Fiorenzo Stirpe, et al.; "Ribosome-Inactivating Proteins from Plants: Present Status and Future Prospects"; Bio/Technology, Apr. 1992; vol. 10, pp. 405-412.
Luigi Barbieri, et al.; "Ribosome-inactivating proteins from plants"; Biochimica et Biophysica Acta; 1993; pp. 237-282.
R.M. Lemoli, et al.; "Positive selection of hematopietic CD34+ stem cells provides 'indirect purging' of CD34- lymphoid cells and the purging effciency is increased by anti-CD2 and anti-CD30 immunotoxins"; Bone Marrow Transplantation; 1994; pp. 465-471.
I.J. Diel, et al.; "Detection of Tumor Cells in Bone Marrow of Patients with Primary Breast Cancer: A Prognostic Factor for Distant Metastasis"; Journal of Clinical Oncology; 1992; pp. 1534-1539.

Arne T. Muklebust, et al.; "Eradication of Small Cell Lung Cancer Cells from Human Bone Marrow with Immunotoxins"; Cancer Research; 1993; pp. 3784-3788.
William P. Peters, et al.; "High-Dose Chemotherapy and Autologous Bone Marrow Support as Consolidation After Standard-Dose Adjuvant Therapy for High-Risk Primary Breast Cancer"; Journal of Clinical Oncology; Jun. 1993; vol. 11, No. 6, pp. 1132-1143.
James O. Armitage, M.D.; "Bone Marrow Transplantation"; New England Journal of Medicine; Mar. 24, 1994; vol. 330, No. 12, pp. 827-838.
Thomas J. Moss, et al.; "Contamination of Peripheral Blood Stem Cell Harvests by Circulating Neuroblastoma Cells"; Blood; 1990; vol. 76, No. 9, pp. 1879-1883.
Malcolm K. Brenner, et al.; "Gene-marking to trace origin of relapse after autologous bone-marrow transplantation"; Lancet; 1993; pp. 85-86.
Amy A. Ross, et al.; "Detection and Viability of Tumor Cells in Peripheral Blood Stem Cell Collections From Breast Cancer Patients Using Immunocytochemical and clonogenic Assay Techniques"; Blood; vol. 82, No. 9, pp. 2605-2610.
John G. Gribben, M.D., et al.; "Immunologic Purging of Marrow Assessed by PCR Before Autologous Bone Marrow Transplantation for B-Cell Lymphoma"; New England Journal of Medicine; Nov. 28, 1991; vol. 325, No. 22, pp. 1525-1533.
Elizabeth J. Shpall, et al.; "Release of Tumor Cells from Bone Marrow"; Blood; Feb. 1, 1994; pp. 623-625.
Wolfram Brugger, et al.; "Mobilization of Tumor Cells and Hematopoietic Progenitor Cells Into Peripheral Blood of Patients With Solid Tumors"; Blood; 1994; vol. 83, No. 3, pp. 636-640.
Ger J. Strous, et al.; "Mucin-Type Glycoproteins"; Critical Reviews in Biochemistry and Molecular Biology; 1992; pp. 57-92.
Lou de Leij, et al.; "The Use of Monoclonal Antibodies for the Pathological Diagnosis of Lung Cancer"; In: H.H. Hansen (ed), Lung Cancer: Basic and Clinical Aspects; Boston: Martinus Niijhoff Publishers, 1986; pp. 31-48.
Aslak Godal, et al.; "Immunotoxins directed Against the High-Molecular-Weight Melanoma-Associated Antigen. Identification of Potent Antibody-Toxin Combinations"; Int. J. Cancer; 1992; pp. 631-635.
V.D. Courtenay, et al.; "An In Vitro Colony Assay For Human Tumours Grown in Immune-Suppressed Mice and Treated In Vivo with Cytotoxic Agents"; Br. J. Cancer; 1978; pp. 261-268.
M.Y. Wang, et al.; "An effective immunomagnetic method for bone marrow purging in T cell malignancies"; Bone Marrow Transplantation; 1992; pp. 319-323.
Arne T. Myklebust, et al.; "Comparison of Two Antibody-based Methods for Elimination of Breast Cancer Cells from Human Bone Marrow"; Cancer Research; 1994; pp. 209-214.
Connie J. Eaves; "Peripheral Blood Stem Cells Reach New Heights"; Blood; 1993; pp. 1957-1959.
Elizabeth J. Shpall, et al.; "Transplantation of Enriched CD34-Positive Autologous Marrow Into Breast Cancer Patients Following High-Dose Chemotherapy: Influence of CD34-Positive Peripheral-Blood Progenitors and Growth Factors on Engraftment"; Journal of Clinical Oncology; 1994; vol. 12, No. 1, pp. 28-36.
Kemmer et al, J. of Immuno. Mths, 147(2), 197-200, 1992.
Biofutur et al., 1993, *Technoscope,* Issue 56, p. 1-11.
Bosnes et al., 1989, *Immunomagnetic separation of infiltrating T lymphocytes from brain tumors*, Journal of Neurosurgery, 71:218.
Dynal technical document, "Immunomagnetic Separations Using Dynabeads®", 1989.
Dynal technical document, "Dynabeads® M-450 CD4 (T-helper/inducer cells)", 1990.
Dynal technical handbook, "General Cell Separation", 1992.
George et al., 1992, *Rapid Isolation of Human Endothelial Cells from Whole Blood Using S-Endol Monoclonal Antibody Coupled to Immuno-Magnetic Beads: Demonstration of Endothelial Injury after Angioplasty,* Thrombosis and Haemostasis, 1992, vol. 67:147.
Ho et al., 1989, *Double-marker analysis of B lymphocyte subsets using a combination of immunofluorescence and resetting with immunomagnetic beads,* Medical Laboratory Sciences, 46:324.
Hovdenes et al., 1989, *Expression of Activation Markers on $CD4^+$ and $CD8^+$ Cells from Synovial Fluid, Synovial Tissue, and Peripheral Blood of Patients with Inflammztory Arthritides,* Scand. J. Immunol., 29:631.
Kvale et al., 1988, *Rapid Selection of Cultured Cells with Increased Expression of a Membrane Marker* (*Secretory Component*), International Journal of Cancer, 42:638.
Leven et al., 1991, *Immunomagnetic bead isolation of megakaryocytes from guinea-pig bone marrow: effect of recombinant interleukin-6 on size, ploidy and cytomplasmic fragmentation,* British Journal of Haematology, 77:267.
Rana et al., 1988, *Paramagnetic microspheres as immunological markers for light and electron microscopy*, Journal of Immunological Methods, 115:209.
Kessler, et al., "Large-scale Purification and Characterization of CD34-Positive Hematopoieticprogenitor Cells", Navel Medical Research Institute, Immunobiol. & Transplantation Dept., Bethesda, MD.
Derwent Accession No. 93-173192, Toyobo KK: "Sensitivity detection of ligand-receptor reaction-by combining fluorescent fine particles with objective substance, passing mixt. through flow cytometer, counting number of agglomerates etc." & JP,A5107249, 930427, DW9321, Apr. 27, 1993.
Kessler et al, "Large-scale purification and characterization of CD-34-positive hematopoietic progenitor cells," Naval Medical Research Institute, Immunobiol. & Transplantation Dept. Bethesda, MD. Blood, 1987; 70:321a.
Decision Revoking the European Patent No. EP-B-0660930; Article 102(1) Opposition Division; Nov. 18, 2003.
Harlow, E., et al., "Antibodies: A laboratory manual," Cold Spring Harbor Laboratory (1988).
Sixma, J.J., "Thrombosis and haemostatis," Journal of Immunological Methods, from Opposition Proceedings, European Patent No. 0660930 of Fodstad and Kvalheim, Annex 2, Frank B. Dehn & Co., Aug. 2, 2000.
Harlow and Lane, Selected pages from Antibodies: A Laboratory Manual (1988) Cold Spring Harbor Laboratory, Eds. Chapter 10, p. 420, Chapter 12, pp. 496-497; Chapter 14, p. 586-587, and p. 689.
Morgan, Selected pages from Current Protocols in Cell Biology (no date) John Wiley and Sons, Inc.6.2.11-6.2.12.

METHOD FOR DETECTION OF SPECIFIC TARGET CELLS IN SPECIALIZED OR MIXED CELL POPULATION AND SOLUTIONS CONTAINING MIXED CELL POPULATIONS

Matter enclosed in heavy brackets [ ] appears in the original patent but forms no part of this reissue specification; matter printed in italics indicates the additions made by reissue.

This is a Divisional of application Ser. No. 08/403,844, filed Apr. 18, 1995, which is a U.S. National Stage filing of PCT/NO93/00136, filed Sep. 10, 1993 and amended on Apr. 14, 1994, claiming priority from PCT/NO92/00151, filed Sep. 14, 1992, which applications are incorporated herein by reference.

The present invention relates to an immunomagnetic method for detection of specific target cells in cell populations and solutions of cell populations. The invention also relates to a kit for performing the method in different cell populations.

In biology, biochemistry and adjacent fields it is considerable need for methods in which chemical entities are linked together. Such methods have an increasing importance in research regarding both normal and abnormal cell populations. Especially when solid supports are used cells can be immobilized, detected and isolated and purified. Furthermore, the cell content may be examined using a range of sofisticated methods. It is also of importance to be able to isolate the cells in viable forms.

Affinity binding is a sofisticated way of linking chemical/biochemical entities together. In such a method a pair of binding partners, which for example are attached to the substances to be linked, bind to each other when brought in contact. One of the binding partners in such a linkage may be represented by a molecule on the cell surface. Several such binding partner systems are known, such as antigen-antibody, enzyme-receptor, ligand-receptor interactions on cells and biotin-avidin binding, of which antigen-antibody binding is most frequently used. A hapten/anti-hapten binding pair has also recently been suggested (WO 91/01368).

When such methods are used for isolation of specific cells, which are the subject for further various examinations, it is necessary to reverse the linkage without producing destructive effects on the binding partners, which ideally should recover their function upon returning to the original conditions. This is not always the case, although it is proposed a method for adequately cleaving antigen/anti-antigen and hapten/anti-hapten linkages (PCT/EP91/00671, PCT/EP90/01171).

Methods are known in which one of the binding partners is attached to an insoluble support, such as paramagnetic particles, and by which isolation of target cells in a mixed cell population is performed as negative isolation or positive isolation. In a negative isolation procedure the unwanted cells can be removed from the cell preparation by incubating the cells with antibody-coated particles, specific for the unwanted cells. Following the incubation the cell/antibody/particle-complex can be removed using the particles, leaving the wanted target cells behind. This result is often not satisfactory, since the wanted cells are left in the cell population, more or less purified, and also since the intention of the isolation procedure is to examine and/or perform further studies on the specific target cells. Attempts have been made to use particles for positive isolation, in which the wanted target cells are removed from the mixed cell population. These procedures have, however, been directed to certain target cells and are not suited for all target cell systems. A positive isolation procedure involving the hapten/anti-hapten linkage system has recently been proposed (PCT/EP90/01171) and also a method for isolating haemopoietic progenitor cells from bone marrow (PCT/EP90/02327). The latter is directed to use a combination of positive and negative selection for the purpose of isolating and possibly growing specific cells, i.e. haematopoietic progenitor cells, in the bone marrow, and is dependent upon removal of the particles.

PCT/EP90/01171 relates to a method of connecting target cells to an insoluble support by using the abilities of hapten, anti-hapten antibodies and anti-cell antibodies to bind to each other, thus constructing a linkage between the insoluble support, i.e. particle, and the target cell, consisting at least of hapten and anti-hapten antibody or combinations of hapten and anti-hapten antibodies and anti-anti-hapten antibodies or secondary anti-cell antibodies. The later cleavage of the complex is performed by again exposing it to hapten or hapten analogue. Thus the constructed link always consists of hapten in addition to 1 or more elements. The method is directed to unspecified target cells and is directed to isolation of target cells and release of the insoluble support.

There is a need for a simple linkage to connect a target cell to an insoluble support, which do not involve compounds of a rather unspecified haptene-group, and which is directed to detection of specific target cells, with a minimum of unspecific cell association and which render unnecessary a later cleavage between the insoluble support and the specific target cell.

Thus the object of the present invention is to detect for diagnostic purposes specific target cells when used in a blood and bone marrow, without the problem with unspecific binding to normal cells. It represents a sensitive detection method for a variety of cells types, such that a high number of cells can be readily screened in the microscope and the procedure is rapid and simple. Furthermore, the present method can be used for isolation of cells for biochemical, biological and immunological examination, and for studying of specific genes at the nucleotide or protein level, in addition to culturing the cells, without the need for cleaving the cell-particles complex. A further object of the invention is to provide a kit for performing the method as characterized in the claims.

The intensions of the inventions are obtained by the method and kit characterized in the enclosed claims.

The method for immunomagnetic detection of target cells in a mixed cell population and physiological solutions containing cell populations is suitable for detection, but may also be used in positive isolation of specific types of both normal cells and patogenic cells. The method creates a linkage between a specific target cell and an insoluble support, such as paramagnetic particles, which consists of one or two elements. The particle is either coated with an anti-cell antibody of murine or human origin, directed to the specific antigen determinants in the membranes of the wanted target-cells, or the particles are coated with a polyclonal anti-mouse or anti-human antibody capable of binding to the Fc-portions of the specific anti-cell antibody directed to the antigen determinants in the target-cell membranes. Instead of using the polyclonal anti-mouse/anti-human antibody for coating the particles, a monoclonal rat anti-mouse/anti-human antibody may be used. This last antibody, due partly to its monoclonal origin, may provide a more specific binding to the anti-cell antibody and reduce the risk for possible cross-reactions with other cells in solutions, such as blood. Furthermore, incubation of the cell suspension with a mild detergent and/or second set of antibodies or antibody fragments, prelabeled or not with fluorescent agents, metallocolloids, radioisotopes, biotin-complexes or certain enzymes allowing visualization, will dramatically increase the specificity of the method.

In the following a more detailed disclosure of the method is presented, using cancer cells as the target-cells for detection and possible isolation. The method is, however, not limited to cancer cells and the disclosure shall not limit the method to this particular field of use, since the method is suitable within a range of cytological research areas.

In the management of cancer patients, the staging of the disease with regards to whether it is localized or if metastatic spread has occurred to other tissues, is of utmost importance for the choice of therapeutic alternative for the individual patient. Malignant cells spread by direct invasion into the surrounding tissue, through the lymphatics or by the distribution of tumor cells in the blood to distant organs, including the bone marrow and the central nervous system and the cerebrospinal fluid.

Detection of metastatic tumor cells has, until recently, relied on morphological methods using light and electron microscopy on biopsied tumor specimens, on smears of bone marrow and peripheral blood, and on slides prepared after cytosentrifugation of various body fluids. Since the advent of monoclonal antibodies recognising antigens predominantly expressed on the surface of different types of malignant cells, the identification of metastatic cells has, to an increasing extent, also involved immunocytochemistry and immunofluorescence. Thus, slides prepared from biopsied tumors or cytosentrifugates have been treated with monoclonal antibodies, and the binding of these to the tumor cells is visualized colorimetrically or by fluorescence. The latter method requires the use of a fluorescence microscope, alternatively preparing a cellsuspension an use a flow cytometer.

The previous methods suffer from limited sensitivity and/or specificity, and is usually laborious and time consuming, also requiring a high degree of expertise. Flow-cytometric examinations also involve expensive equipment.

The morphological methods for the detection of tumor cells in blood and bone marrow are much less sensitive than methods involving immunocytochemistry and immunofluorescence (Beiske et al., Am. J. Pathology 141 (3), September 1992). Also the latter methods are, however, inadequate in cases where the tumor cells represent less than 1% of the total number of nucleated cells. Flow cytometry may provide better sensitivity than the methods involving the use of a microscope, but requires the availability of a high number of cells, and also involves several technical difficulties. Thus, aggregation of cells may cause problems, and the method does not provide possibilities to distinguish between labeled tumor cells and unspecifically fluorescing normal cells.

The invention allows for a very sensitive detection of, for example, metastatic tumor cells, since a high number of cells can readily be screened in the microscope and the attached magnetic beads are easily recognisable. The monoclonal antibodies used bind with sufficient specificity to, for example, tumor cells and not to other cells than the target-cells present in mixed cell suspensions, like blood, bone marrow, and in other tumor manifestations, such that all cells with attached beads represent the target-cells. In addition, the procedure is rapid and simple, and can be performed by any investigator with access to a conventional microscope.

The novel method involves the binding of monoclonal antibodies, e.g. of murine or human origin, that specifically recognize antigens present on tumor cells, and not on the normal cells in question, or for other purposes to specified subpopulations of normal cells, to paramagnetic particles, either directly or to beads first covered with antibodies specifically recognizing the respective antibodies, or the Fc-portion of IgG antibodies, that bind to the tumor cells. The cell binding antibodies may be of the IgG or IgM type or being a fragment of ab IgG or IgM. Examples of used anti-target-cell antibodies may be those directed against groups of antigen determinants, for example CD56/NCAM antigen (MOC-1), Cluster 2 epithelial antigen (MOC-31), Cluster 2 (MW~40 kD) antigen (NrLu10) (Myklebust et al. Br. J. Cancer Suppl. 63, 49-53, 1991), HMW-melanoma-associated antigen (9.2, 27) (Morgan et al., Hybridoma, 1, 27-36, 1981), 80 kD, Sarcoma-associated antigen (TP1 & TP3) (Cancer Res. 48, 5302-5309, 1988), mucin antigens (Diel et al., Breast Cancer Res. Treatm., 1991), or EGF-receptor antigen (425.3) (Merck), in addition to the anti-pan-human antibody (Bruland et al., unpublished), which is suitable for detecting human cells among animal cells. The 425.3 antibody is directed towards antigens in both normal and malignant cells. Antibodies can furthermore be directed against growth factor receptors, for example EGF-receptor, PDGF (A and B) receptor, insuline receptor, insuline-like receptor, transferrin receptor, NGF and FGF receptors, group of integrins, other adhesion membrane molecules and MDR proteins in both normal cells and abnormal cells, and antigens present on subpopulations of normal cells, in addition to oncogenic products, expressed on the membranes of normal and malignant cells and on malignant cells alone, for example Neu/erb B2/HER2. As for the malignant cells, these may be breast, ovarian and lung carcinoma cells, melanoma, sarcoma, glioblastoma, cancer cells of the gastrointestinal tract and the reticuloendothelial system, or the target-cells may be associated with non-neoplastic diseases, such as cardiovascular, neurological, pulmonary, autoimmune, gastrointestial, genitourinary, reticuloendothelial and other disorders. Furthermore, the malignant cell population may be located in bone marrow, peripheral blood, come from pleural and peritoneal effusions and other body fluid compartments, such as urine, cerebrospinal fluid, semen, lymph or from solid tumors in normal tissues and organs, for example liver, lymph nodes, spleen, lung, pancreas, bone tissue, the central nervous system, prostatic gland, skin and mucous membranes. A more complete list of the antigen determinants and the corresponding antibodies or antibody fragments used in the present improved method is presented in Table 1.

The method comprises attachment of the antibodies directly to the paramagnetic particles, or the attachment can take place by attachment to surface-bound antibodies, such as polyclonal anti-mouse antibodies, monoclonal rat anti-mouse antibodies or monoclonal anti-human antibodies, specifically recognizing the Fc-portion of the said individual antibodies. The antibody-coated paramagnetic beads are then mixed with the suspension of cells to be examined and incubated for 5-10 min to 2 h, preferably for 30 min at 0-25° C., preferably at 4° C., under gentle rotation. The present method may also be performed in a changed order of steps, in that the free target-cell antibodies are added to the cell suspension, incubated for 5-10 min to 2 h, preferably 30 min, at 0-20° C., preferably 4° C., under gentle rotation. The paramagnetic particles, pre-coated with anti-mouse or anti-human antibodies are then added to the incubated cell suspension, as described above, and the resulting suspension subjected to a further incubation of 5-10 min to 2 h, preferably 30 min, at 0-25° C., preferably 4° C. under gentle agitation.

Samples of the cell suspension are then transferred to a cell containing device, and the fraction of cells with attached beads relative to the total number of cells is determined under light microscopy. The number of antibody-coated beads added to the cell suspension should be between 0.5-10 times the number of target cells. When this number is unknown, the amount of coated beads added should be 1-10% of the total number of cells.

For specific purposes, and in the cases where the density of the target-cells is low, for example malignant cells, or the target-cells represent a very low fraction of the total number of cells (≦1%), the target cells can be positively separated from non-target cells in a magnetic field. The isolated target cells, can then be enumerated microscopically and the fraction of target cells relative to the total number of cells in the initial cell suspension can be calculated. Moreover, the target-cells may be characterized for the presence of specific biochemical and biological features. Of particular importance will be the use of such cells for studies in molecular biology. In contrast to the above cited methods of the prior art, the present method allows studies and growth of the target-cells without performing a cleavage of the paramagnetic particle-target cell linkage. For several purposes it is of interest to examine specific genes in a pure population of target cells at the DNA, mRNA and protein level, both in tumor biopsies as well as in tumor cells present in blood, bone marrow and other body fluids, for example urine, cerebrospinal fluid, semen, lymph, or from otherwise normal tissues and organs, for example liver, lymph nodes, spleen, lung, pancreas, bone tissues, central nervous system, prostatic gland, skin and mucous membranes, and in other areas of cytological research activity.

With the methods of prior art, signals obtained on Southern, Northern and Western blots represent the normal cells as well as the tumor cells in the biopsy. If a single cell suspension is first prepared from the tumor material, and the tumor cells are then positively immunomagnetically detected and separated, any gene studies performed on this material would represent the target-cells only. This also relates to for example malignant cells present in mammalian tissues, for example in bone marrow, peripheral blood, pleural and peritoneal effusions, and other body fluids, for example urine, cerebrospinal fluid, semen and lymph. Studies involving polymerase chain reaction (PCR) methodology will also gain in specificity and reliability when performed on pure tumor cell populations obtained by the new method.

The application of the new method steps may differ depending on type of tissues to be examined.

a) Tissue from solid or needle tumor biopsies is prepared mechanically or with mild enzymatic treatment into a single cell suspension, to which the primary, specific antibodies or antibody fragments are added directly or after washing the cell suspension with phosphate buffered saline or culture medium with or without serum, such as fetal calf serum, bovine, horse, pig, goat or human serum.

b) If the material is a sample of pleural or ascitic effusion, cerebrospinal fluid, urine, lymph or body fluids such as effusions in the joints of patients with various forms of arthritis, the specific antibodies or antibody fragments are either added to the samples directly, or after centrifugation with or without washings before or after the cells in the samples are spun down and brought back into suspension.

c) If the material consists of blood or bone marrow aspirate, the mononuclear cell fraction is isolated by gradient sentrifugation on e.g. Lymphoprep before washing, resuspension, and addition of the appropriate antibodies or antibody fragments.

The procedure conditions for a) and b) are established, as exemplified by results obtained in successful experiments as those described below.

For c) the results have been found to be influenced by a high number of factors which have been examined in detail. Among these are antibody concentration, the ratio of the number of paramagnetic particles versus number of cells, incubation times and volumes, type of incubation medium, and the pH level. The particle to mononuclear cell ratio in all experiments should be in the range of 0.5/1-2/1, depending on the binding affinity of the primary specific antibodies or fragments.

A major problem has been unspecific attachment to normal blood or bone marrow cells of particles coated with either sheep or rat anti-mouse antibodies alone, or in addition with the specific antibodies. Experiments have shown that the unspecific binding is equally high without the presence of the specific antibodies, indicating that the problem is not caused by cross-reactivity of the targeting antibodies to normal cells. The possibility that the less than optimal specificity could be caused by ionic binding has been ruled out. Another possibility was that subpopulations of normal cells of the B-lineage might adhere to the particle-antibody complexes. However, immunomagnetic removal of B-cells from the cell suspension before adding the specific antibodies/antibody-particle complexes did not improve the specificity of the latter.

The problem with the procedure used on isolated mononuclear fractions of bone marrow and peripheral bllod, that some non-target cells might also bind paramagnetic particles, has been circumvented or overcome. Thus with sheep-anti-mouse antibody coated particles alone or with specific antibodies the number of particles unspecifically attached to a low fraction mononuclear blood of bone marrow cells was reduced from an average of 10 to about 1 and in paralell the fraction of normal cells with particles decreased from 1-2% to 0.5-1% or less.

Evidence has been obtained that the problem may be caused by hydrophobic forces associated with the antibodies bound to the paramagnetic particles. Methods for reducing this hydrophobicity is thus claimed. One such method is preincubation of the antibody-coated particles and the cell suspension with mild detergents in suitable concentrations, for example Tween 20™ in concentrations of less than 0.1% for 30 minutes at 4° C. When possible selection of the target cells is warrented, the cell suspension should contain a low concentration of the detergent, e.g. 0.01% of Tween 20™. In several experiments this procedure has almost eliminated or dramatically reduced the problem of unspecific binding seen with the mononuclear cell fractions from blood or bone marrow.

The other improvement which, if found warrantied, may be used together with the detergent step as follows:

After incubation of the cell suspension with the primary antibodies or antibody fragments and the antibody-coated paramagnetic particles as described in previously, the cell suspension is incubated with a second set of antibodies or antibody fragments directed against other extracellular or against intracellular determinants of the target cells, with our without pretreatment with cell fixatives such as formaldehyde or alcohols. These antibodies or their fragments should have been prelabeled by fluorescent agents, metallocolloids, radioisotopes, biotin-complexes or enzymes like peroxidase and alkaline phosphatase, allowing visualization by per sc known methods in the microscope and/or a suitable counting device.

The target cells will both be visualized with the latter method and have bound particles to their surface, and can thus be enumerated.

To simplify the distinction between non-target and target cells, the cell suspension can before the second visualization step either be subjected to cytospin centrifugation or portions of the suspension are attached to caoted glass slides on which the particle-bound cells will be spread out in a thin layer, facilitating the recognition of the double-"stained" cells.

For use in the new procedure, kits will contain for example precoated paramagnetic particles prepared for each monoclonal antibody. In another embodiment the kits contain paramagnetic particles pre-coated with IgG isotype specific anti-mouse or anti-human antibody as one part of it, and different target cell-associated, for example tumor cell, antibodies as another part. In a third embodiment the kit contains paramagnetic particles precoated with specific anti-Fc antibodies, such as polyclonal anti-mouse, or monoclonal rat anti-mouse, or anti-mouse, or anti-human antibodies, capable of binding to the Fc-portion the target-cell associating antibodies, bound to specific anti-target-cell antibodies. In a further embodiment the kit contains other specific antibodies or antibody fragments directed against antigens/receptors within or on the wanted target-cells, where said antibodies or antibody fragments are conjugated to peroxidase, alkaline phosphatase, or other enzymes, together with relevant substrates to such enzymes, or where said antibody or antibody fragment is bound to non-paramagnetic particles with specific colours or with bound enzymes such as peroxidase and alkaline phosphatase.

The present method will in the following be illustrated by model experiments, examples of the usefulness of the new method and examples of practical applications. These examples shall not be regarded as in any way limiting the invention.

Model Experiments

1. Binding of antibody-based complexes to tumor cell lines with the new procedure To determine antibody concentrations and optimal conditions for the binding of antibody-paramagnetic particle complexes to tumor cells, a large panel of cancer cell lines was used. The paramagnetic beads were bound to the cells, either by coating the specific antibodies to sheep-anti-mouse antibody (SAM)-coated paramagnetic particles, or by first incubating the cells with the specific antibodies, washing, followed by a second incubation with SAM-coated particles. The results of these experiments are given in Tables 2a and 2b, in which + indicates binding of several beads to all cells, (+) indicates either a lower number of beads bound to each cell, or that not all the tumor cells had beads attached to their surface, whereas – reflects no binding, and (–) indicates very weak binding.

2. For detection of tumor cells in the mononuclear fraction of bone marrow or peripheral blood, model experiments were performed where specific antibodies and SAM-coated paramagnetic particles were added either to such mononuclear cells or to a cell suspension where a different number of cancer cells from in vitro cultivated cell lines were added to said mononuclear cells. In some experiments, either the mononuclear cells, or the malignant cells were prestained with a fluorescent dye, to be able to distinguish beteween the two types of cells. In all experiments, non-binding primary antibodies, and/or sheep-anti-mouse antibody-coated beads were used separately as controls.

TABLE 2a

| | | Cell lines | | | | | | | |
|---|---|---|---|---|---|---|---|---|---|
| Antibodies | | MCF-7 | SKBR3 | T47D | MDA231 | MDA435 | DU145 | FMEX-1 | LOX |
| NrLu10 | IgG2b | | + | + | (+) | (+) | + | | |
| Moc31 | IgG1 | + | + | + | (+) | (+) | + | | |
| Moc1 | IgG1 | | | (+) | (+) | + | | | |
| 12H12 | IgG1 | | + | + | | + | + | | |
| 2E11 | IgG3 | + | + | + | | + | + | | |
| 5A6 | IgG1 | | (+) | + | | | | | |
| 5F2 | IgM | | | (+) | | | | | |
| CC3 | IgG2a | – | – | – | | | | – | |
| CC1 | IgM | | | – | | | | (+) | |
| CU18 | IgG1 | – | – | – | | | | | |
| CU46 | IgG1 | (+) | – | – | | | | | |
| 7F11 | IgG1 | – | – | + | | | – | – | – |
| D7 | IgG3 | | | (+) | | | | | |
| E4SF | IgG1? | | + | + | | | (–) | – | 50%+ |
| 425-3 | | | | + | | | | – | + |
| 9.2.27 | | | | | | | | + | + |
| MUC18 | | | – | | | | – | – | – |
| 2g12 | IgG1 | | | | | | | + | |
| 4b7 | IgG1 | | | | | | | + | |
| BM2 (=2F11) | | | | | | | | | |
| BM7 (=7F11) | | | | | | | | | |
| TP-3 | | | | | | | | | |
| TP-1 | | | | | | | | | |
| CEA | | | | | | | | | |
| GINTES | IgG | | | | | | | | |
| 3C9 | IgM | | | | | | | | |
| HH8 | IgM | | | | | | | | |
| 5F4 | IgM | | | | | | | | |
| 3F1 | IgG1 | | | | | | | | |

TABLE 2b

| | | Cell lines | | | | | | | |
|---|---|---|---|---|---|---|---|---|---|
| Antibodies | | PM1 | MA-11 | CRL1435 | CRL1740 | H-146 | Co1o205 | 786-0 | WIDR |
| NrLu10 | IgG2b | + | + | + | + | + | + | – | |
| Moc31 | IgG1 | + | + | + | + | + | + | + | + |
| Moc1 | IgG1 | | | | | + | – | | |
| 12H12 | IgG1 | + | + | (+) | | – | – | – | |
| 2E11 | IgG3 | (+) | + | – | + | – | – | – | |
| 5A6 | IgG1 | + | + | | | | | | |
| 5F2 | IgM | | | | | | | | |

TABLE 2b-continued

| Antibodies | | Cell lines | | | | | | | |
|---|---|---|---|---|---|---|---|---|---|
| | | PM1 | MA-11 | CRL1435 | CRL1740 | H-146 | Co1o205 | 786-0 | WIDR |
| CC3 | IgG2a | | | | | – | | – | |
| CC1 | IgM | | | | | (+) | | – | |
| CU18 | IgG1 | | | | | – | | – | |
| CU46 | IgG1 | | | | | – | | – | |
| 7F11 | IgG1 | (+) | + | – | | – | – | | – |
| ID7 | IgG3 | | | | | – | | | – |
| E4SF | IgG1? | + | + | + | + | – | – | | – |
| 425-3 | | | | | | | | | |
| 9.2.27 | | | | | | | | | |
| MUC18 | | – | | | | | | | |
| 2g12 | IgG1 | | | | | – | | – | |
| 4b7 | IgG1 | | | | | – | | – | |
| BM2 (=2F11) | | + | + | | | | | | |
| BM7 (=7F11) | | + | | | | | | | |
| TP-3 | | | | | | | | | |
| TP-1 | | | | | | | | | |
| CEA | | | | | | | | | |
| GINTES | IgG | | | | | + | | | – |
| 3C9 | IgM | | | | | – | | | – |
| HH8 | IgM | | | | | – | | | – |
| 5F4 | IgM | | | | | – | | | – |
| 3F1 | IgG1 | | | | | – | | | – |

In several experiments some unspecific binding to the mononuclear cells was observed, which was found to be unrelated to the nature of the specific antibody, and which was equally pronounced with SAM-coated particles alone. The magnitude of this unspecific binding varied from almost 0 to a level between 0.5-2%. This unspecific binding was almost eliminated by mild treatment with detergent, (Tween 20) performed to reduce the problem of hydrophobic cell interactions.

EXAMPLES OF THE USEFULNESS OF THE NEW PROCEDURE

1. Detection of micrometastic neoplastic disease in blood and marrow

Early and reliable diagnosis of spread of cancer cells to blood and/or bone marrow has become increasingly important for the choice of optimal therapy, possibly curative in many types of cancer, including carcinomas, as described in application Example 1. Similar procedures for malignant melanoma, sarcoma, neuroblastoma and several other cancers have been established or are under development.

2. Detection of malignant cells in pleural or ascitic effusions, and in urine

The nature of such effusions may represent an important diagnostic problem, particularly when a low number of cancer cells are present together with normal reactive or epithelial cells. In several cases a definite diagnosis has been rapidly made with the new method, in cases where conventional cytological examination has been negative or inconclusive. A similar advantage can be found in cases of cancer in the kidneys or in the urinary tract and bladder.

3. Detection of neoplastic cells in the cerebrospinal fluid

As the systemic treatment of many cancer types have improved, the frequency of cases with symptom-giving brain metastases have significantly increased, and in parallell with this, the necessity for early detection of such spread. With the use of the new procedure even a low number of malignant cells can easily be identified, permitting intervention with therapeutic alternatives at an early stage of intracranial tumor manifestations.

4. Diagnosis of cancer in biopsied tissue

When cancer is suspected, and tissue biopsies are obtained by surgical procedures or by e.g. needle biopsies, a much more simple and rapid diagnosis can be made with the new method, used on prepared cell suspensions, compared to conventional morphological or immunohisto- or cytochemical procedures.

Distinction between several alternative cancers can be made by the use of the appropriate antibodies.

5. Identification of prognostic indicators

Since the expression of several membrane molecules have been shown to correlate with progression of the malignant disease in several cancers, the present method can be used to identify prognostic indicators, for example as described in application Example 2.

6. Identification of cells indicative of specific diseases or of disease progression or state In various types of rheumatoid diseases (such as rheumatoid arthritis), as well as in allergic, autoimmune, and cardiovascular diseases, identification of the systemic or local presence of specific subpopulations of cells is important for diagnosis and for determining the stage of the disease. Rapid detection of such cell populations with the new method is therefore of considerable diagnostic and therapeutic importance.

7. Detection of subpopulations of normal cells

For several purposes, it will be important to detect the fraction of a particular subpopulation of normal cells in a population. This applies e.g. to liver biopsies where the identification of cells expressing the biliar epithelial antigen, may be of importance. Similarly, the identification, and possible isolation of specific endothelial cells from a cell suspension prepared from various normal tissues may be warranted.

Several of the cell membrane molecules mentioned in sections 1-6 may also be used as targets for immunotherapy with several types of activiated killer cells or e.g. with immunotoxins. The identification with the new method of expression of such molecules is, therefore, also of value for determining in which cases such types of therapy should be used.

EXAMPLES OF A PRACTICAL APPLICATION OF THE METHOD

Example 1

To diagnose spread of cancer cells in blood and/or bone marrow at an early stage, we have used in the new procedure the MOC-31, NrLu10, BM2, BM7, 12H12, and MLuCl anti-carcinoma antibodies to determine whether or not micrometastatic disease from breast, lung, colorectal, and prostate cancer might be sensitively identified in such body fluids. The successful results with these antibodies have significant clinical implications.

Example 2

The expression of serveral cell membrane molecules have been shown to correlate with progression of the malignant disease in several types of cancer. The detection of binding of such antibodies to respective antibodies can therefore be used to obtain information of high prognostic value. Among such antigens are a high number of adhesion molecules, carbohydrate antigens, glycolipids, growth factor receptors and carcinoma markers listed below. We have, with the new procedure identified the binding of particle-antibody complexes to CD44-variants, E-cadherin, $Le^y$, CEA, EGF-r, transferrin receptor, MUC-1 epitope, LUBCRU-G7 epitope, prostate cancer antigen, UJ13A epitope, $\beta_2$-microglobulin, HLA-antigens, and apoptosis receptor.

Example 3

Two liters or pleural diffusion from a patient supposed to suffer from malignant melanoma was obtained. After centrifugation, the cells were suspended in a volume of 2 ml of RPMI with a 10% fetal calf serum, incubated with 9.2.27 anti-melanoma antibody (10 μg/ml) at 4° C. for 30 min, washed and again incubated with Dynabeads™ SAM M450/IgG2A at 4° C. for 30 min. The cell suspension was then examined under a microscope for determining the fraction of cells with paramagnetic cells attached to their surface. The diagnosis of malignant melanoma was confirmed, as about 10% of the cells had a significant number of particles rosettes.

Example 4

Biopsied tissue was obtained from a subcutaneous tumor in a case with clinical indications of either small cell lung cancer or a malignant melanoma. A single cell suspension was prepared from the biopsy, divided in 2 fractions, one incubated with the 9.2.27 anti-melanoma antibody, and the other with MOC-31 anti-carcinoma antibody (both at 10 μg/ml). The incubation was similar to that used in the example above. None of the cells incubated with the melanoma antibody bound any beads, whereas all tumor cells incubated with MOC-31 were positive.

Example 5

Biopsied tissue from a patient suspected to have malignant melanoma was examined by preparing single cell suspension, incubating with 9.2.27 anti-melanoma antibody, and then following the procedure as above. Most of the cells were positive with a high number of particle-rosettes attached to their membranes.

Example 6

A pleural effusion from a breast cancer patient was studied to examine whether tumor cells could be detected in the fluid. One liter of the fluid was centrifuged, the cells resuspended, and in separate vials incubate with each of 3 different anti-carcinoma antibodies (MOC-31, 2E11, 12H12). After completing the procedure as in the previous example, it was found that most of the cells bound to antibody-coated particles in all 3 cases.

Example 7

A bone marrow suspension obtained from a breast cancer patient was studied to examine whether micrometastic tumor cells could be present. After the preparation of mononuclear cells, these were incubated with the same 3 anti-carcinoma antibodies used in the example above, but in this case the antibodies were first attached to Dynabeads™ SAM IgG paramagnetic particles. After 1 incubation with these directly coated particles, the cell suspension was examined in the microscope, and a high number of cells were found positive with a number of particle-rosettes attached to their membrane.

Similar experiments have been performed in a number of pleural or ascitic effusion and bone marrow from patients with breast cancer.

Example 8

T47D human breast carcinoma cells were incubated for varying lenghts of time with Hoechst fluorescence dye, and the viability of the labeled cells was checked. Varying numbers of labeled breast carcinoma cells were then added to $1\times10^6$ bone marrow cells obtained from healthy volunteers. In different experiments, different concentrations of paramagnetic, monodisperse particles (Dynabeads™ P450) coated with individual anticarcinoma antibodies (NrLu10, MOC31, or 12H12) were added. After incubation for 30 min on ice, samples of the different test tubes were examined in a counting chamber under light and fluorescence microscopy. When the ratio of tumor cells/total nucleated cells was low, the cell suspension was subjected to a magnetic field and the cells with particles attached were isolated before examined in the microscope. It was found that at an optimal ratio of 1-10 paramagnetic beads per tumor cell in the cell mixture, all the tumor cells had from 2-15 beads attached to their surface. The sensitivity of the detection method was close to one target-cell per $10^4$ nucleated cells. In control experiments with labeled tumor cells using antibodies known to have some cross-reativity to normal cells, this cross-reactivity was confirmed with the antibody-coated paramagnetic particles. In experiments with beads without tumor-associated antibody coating, none of the target cells bound any beads.

Similar experiments have been performed both with other breast cancer lines and a small cell lung cancer cell line. Similar sensitivity and specificity were obtained in these experiments.

Example 9

Pleural and ascites fluid from patients with breast cancer and ovarian carcinoma were sentrifuged, the same coated paramagnetic particles used in Example 1 were added, incubated and concentrated in a magnetic field before the suspension was examined under light microscopy. Typically, cells that had the clear morphological features of tumor cells had beads attached, whereas none of the few normal cells bound the antibody-coated beads. In two cases with pleural effusion, an independent morphological examination did not reveal the presence of any tumor cells, whereas a significant number malignant cells were detected by the use of anibody-coated beads. In some cases, tumor cells were separated in a magnetic field and transferred to tissue culture flasks containing growth medium specially prepared for growing breast cancer cells, in attempts to establish permanent cell lines from these cultures. In parallel, cells from the malignant effusions were cultivated directly without positive selection with magnetic beads. In the latter cases, no cell line could be established, whereas in more than 50% of the cases where positively selected tumor cells had been used, cell lines were successfully established.

Example 10

In some cases, bone marrow and peripheral blood obtained from patients with breast cancer were examined with the present procedure by adding antibody-coated paramagnetic beads, incubating for 30 min at 4° C. and concentrating in a magnetic field and by examining the suspension under light microscopy. In both cases binding of the paramagnetic beads to tumor cells, representing 0.1-1% of the nucleated cells in the bone marrow and blood was detected, cells that could not be identified by any other method.

Example 11

Antibodies against certain growth factor receptors or other gene products expressed on the surface of specific cell populations may be used to identify and positively select these cells. Beads coated with anti-transferring receptor antibodies, used in the novel method according to the present invention were shown to represent a rapid, simple and sensitive method for identification of cells expressing the transferrin-receptor.

Example 12

For various purposes isolation of specific populations of normal cells is warranted. Endothelial cells lining the capillary or small vessels in normal or tumorous tissue could be positively selected from cell suspensions prepared from the relevant tissues. The procedure involved the use of beads coated with antibody directed against structures expressed on the endothelial cells, but not on the other normal cells in the cell mixture.

Example 13

Human cells injected into immunodeficient rodents was shown to be present in cell suspensions prepared from tumor xenografts and from various host organs/tissues by employing magnetic particles coated with an anti-pan human antibody.

TABLE 1

LIST OF RELEVANT ANTIGENS AND EXAMPLES OF ASSOCIATED ANTIGEN-BINDING ANTIBODIES

| ANTIGENS | MONOCLONAL ANTIBODIES |
|---|---|
| Adhesion molecules | |
| Fibronectin receptor (α5β1 integrin) | Pierce 36114, BTC 21/22 Calbiochem 341649 |
| Integrin α3β1 | M-Kiol 2 |
| Vitronectin receptor (αγβ3 integrin) | TP36.1, BTC 41/42 |
| Integrin α2 | Calbiochem 407277 |
| Integrin α3 | Calbiochem 407278 |

TABLE 1-continued

LIST OF RELEVANT ANTIGENS AND EXAMPLES OF ASSOCIATED ANTIGEN-BINDING ANTIBODIES

| ANTIGENS | MONOCLONAL ANTIBODIES |
|---|---|
| Integrin α4 | Calbiochem 407279 |
| Integrin α5 | Calbiochem 407280 |
| Integrin αV | Calhiochem 407281 |
| Integrin β2 | Calbiochem 407283 |
| Integrin β4 | Calbiochem 407284 |
| GpIIβIIIα | 8221 |
| ICAM-I (CD54) | C57-60, CL203.4, RR 1/1 |
| VCAM-1 | Genzyme 2137-01 |
| ELAM-1 | Genzyme 2138-01 |
| E-selectin | BBA 8 |
| P-selectin/GMP-140 | BTC 71/72 |
| LFA-3 (CD58) | TS 2/9 |
| CD44 | BM 1441 272, 25.32 |
| CD44-variants | 11.24, 11.31, 11.10 |
| N-CAM(CD56) | MOC-1 |
| H-CAM | BCA9 |
| L-CAM | BM 1441 892 |
| N-CAM | TURA-27 |
| MACAM-1 | NRI-M9 |
| E-cadherin | BTC 111, HECD-1 6F9 |
| P-cadherin | NCC-CAD-299 |
| Tenascin | BM 1452 193, Calbiochem 580664 |
| Thrombospondin receptor (CD36) | BM 1441 264 |
| VLA-2 | A1.43 |
| Laminin receptor | |
| HNK-1 epitope | HNK-1 |
| Carbohydrate antigens | |
| T-antigen | HH8, HT-8 |
| Tn-antigen | TKH6, BaGs2 |
| Sialyl Tn | TKH-2 |
| Gastrointestinal cancer associated antigen ($M_w$ 200 kD) | CA 19-9 |
| Carcinoma associated antigen | C-50 |
| $Le^y$ | MLuCl, BR96, BR64 |
| di-$Le^x$, tri-$Le^1$ | B3 |
| Dimeric $Le^1$ epitope | NCC-ST-421 |
| H-type 2 | B1 |
| CA15-3 epitope | CA15-3 |
| CEA | I-9, I-14, I-27, II-10, I-46, Calbiochem 250729 |
| Galb1-4GlcNac (nL4,6,8) | 1B2 |
| H-II | BE2 |
| A type 3 | HH8 |
| Lacto-N-fucopentanose III (CD15) | PM-81 |
| Glycolipids | |
| $GD_3$ | ME 36.1, R24 |
| $GD_2$ | ME36.1, 3F8, 14.18 |
| $Gb_3$ | 38-13 |
| $GM_3$ | M2590 |
| $GM_2$ | MKI-8, MKI-16, |
| $FucGM_1$ | 1D7, F12 |
| Growth factor receptors | |
| EGF receptor | 425.3, 2.E9, 225 |
| c-erbB-2 (HER2) | BM 1378 988, 800 E6 |
| PDGFα receptor | Genzyme 1264-00 |
| PDGFβ receptor | Sigma P 7679 |
| Transferrin receptor | OKT 9, D65.30 |
| NGF receptor | BM 1198 637 |
| IL-2 receptor (CD25) | BM 1295 802, BM 1361 937 |
| c-kit | BM 428 616, 14 A3, ID9.3D6 |
| TNF-receptor | GEnzyme 1995-01, PAL-M1 |
| NGF receptor | |
| Melanoma antigens | |
| High molecular weight antigen (HMW 250.000) | 9.2.27, NrML5, 225.28, 763.74, TP41.2, IND1 |
| Mw105 melanoma-associated glycoprotein | ME20 |

TABLE 1-continued

LIST OF RELEVANT ANTIGENS AND EXAMPLES OF ASSOCIATED ANTIGEN-BINDING ANTIBODIES

| ANTIGENS | MONOCLONAL ANTIBODIES |
|---|---|
| 100 kDa antigen (melanoma/carcinoma) | 376.96 |
| gp 113 | MUC 18 |
| p95-100 | PAL-M2 |
| Sp75 | 15.75 |
| gr 100-107 | /NKI-bereb |
| MAA | K9.2 |
| $M_w$ 125 kD (gp125) | Mab 436 |
| Sarcoma antigens | |
| TP-1 and TP-3 epitope | TP-1, TP-3 |
| $M_w$ 200 kD | 29-13, 29.2 |
| $M_w$ 160 kD | 35-16, 30-40 |
| Carcinoma markers | |
| MOC-31 epitope (cluster 2 epithelial antigen) | MOC-31, NrLu10 |
| MUC-1 antigens (such as DF3-epitope (gp290 kD)) | MUC-1, DF3, BCP-7 to −10 |
| MUC-2 and MUC-3 | PMH1 |
| LUBCRU-G7 epitope (gp 230 kD) | LUBCRU-G7 |
| Prostate specific antigen | BM 1276 972 |
| Prostate cancer antigen | E4-SF |
| Protate high molecular antigen $M_w$ > 400 kD | PD41 |
| Polymorphic epithelial mucins | BM-2, BM-7, 12-H-12 |
| Prostate specific membran antigen (Cyt-356) | 7E11-C5 |
| Human milk fat globulin | Immunotech HMFG-1, 27.1 |
| 42 kD breast carcinoma epitope | B/9189 |
| $M_w > 10^6$ mucin | TAG-72, CC-49, CC-83 |
| Ovarian carcinoma OC125 epitope ($m_w$ 750 kD) | OC125 |
| Pancreatic HMW glycoprotein | DU-PAN-2 |
| Colon antigen Co17-1A ($M_w$ 37000) | 17-1A |
| G9-epitope (colon carcinoma) | G9 |
| Human colonic sulfomucin | 91.9H |
| $M_w$ 300 kD pancreas antigen | MUSE11 |
| GA 733.2 | GA733, KS1.4 |
| TAG 72 | B72.3, CC49, CC83 |
| Undefined | Oat1, SM1 |
| Pancreatic cancer-associated | MUSE 11 |
| Pancarcinoma | CC49 |
| Prostate adenocarcinoma-antigen | PD 41 |
| $M_w$ 150-130 kD adenocarcinoma of the lung | AF-10 |
| gp160 lung cancer antigen (Cancer Res. 48, 2768, 1988) | anti gp160 |
| $M_w$ 92 kD bladder carcinoma antigen | 3G2-C6 |
| $M_w$ 600 kD bladder carcinoma antigen | C3 |
| Bladder carcinoma antigen (Cancer Res. 49, 6720, 1989) | AN43, BB369 |
| CAR-3 epitop $M_w$ > 400 kD | AR-3 |
| MAM-6 epitope (C15.3) | 115D8 |
| High molecular ovarian cancer antigen | OVX1, OVX2 |
| Mucin epitope Ia3 | Ia3 |
| Hepatocellular carcinoma antigen $M_w$ 900 kD | KM-2 |
| Hepernal epitope (gp43) Hepatocellular carc. ag | Hepema-1 |
| O-linked mucin containing N-glycolylneuraminic acid | 3E1.2 |
| $M_w$ 48 kD colorectal carcinoma antigen | D612 |
| $M_w$ 71 kD breast carcinoma antigen | BCA 227 |
| 16.88 epitope (colorectal carcinoma antigen) | 16.88 |
| CAK1 (ovarian cancers) | K1 |
| Colon specific antigen p | Mu-1, Mu-2 |
| Lung carcinoma antigen $M_w$ 350-420 kD | DF-L1, DF-L2 |
| gp54 bladder carcinoma antigen | T16 |
| gp85 bladder carcinoma antigen | T43 |
| gp25 bladder carcinoma antigen | T138 |

TABLE 1-continued

LIST OF RELEVANT ANTIGENS AND EXAMPLES OF ASSOCIATED ANTIGEN-BINDING ANTIBODIES

| ANTIGENS | MONOCLONAL ANTIBODIES |
|---|---|
| Neuroblastoma antigens | |
| Neuroblastoma-associated, such as UJ13A epitope | UJ13A |
| Glioma antigens | |
| Mel-14 epitope | Mel-14 |
| Head and neck cancer antigens | |
| $M_w$ 18-22 kD antigen | E48 |
| HLA-antigens | |
| HLA Class 1 | TP25.99 |
| HLA-A | VF19LL67 |
| HLA-B | H2-149.1 |
| HLA-A2 | KS1 |
| HLA-ABC | W6.32 |
| HLA-DR, DQ, DP | Q 5/13, B 8.11.2 |
| $\beta_2$-microglobulin | NAMB-1 |
| Apoptosis receptor | |
| Apo-1 epitope | Apo 1 |
| Various | |
| Plasminogen activator antigens & receptors | Rabbit polyclonal |
| p-glycoprotein | C219, MRK16, JSB-1, 265/F4 |
| cathepsin D | CIS-Diagnostici, Italy |
| biliary epithelial antigen | HEA 125 |
| neuroglandular antigen (CD63) | ME491, NK1-C3, LS62 |
| CD9 | TAPA-1, R2, SM23 |
| pan-human cell antigen | pan-H |

We claim:

1. A method for detecting and quantitating a specific living target cell in a cell suspension of a mixed cell population at a sensitivity of one target cell per 100 or more total cells, in a fluid system containing a mixed cell population, or in a single-cell suspension prepared from a solid tissue, with the exception of normal and malignant hematopoietic cells in blood and bone marrow, the method comprising the steps of:

a. coating paramagnetic particles or beads with an antibody or antibody fragment directed against a membrane structure specifically expressed on the target-cell and not on a non-target-cell in the cell mixture;

b. mixing the coated paramagnetic particles or beads with the cell suspension containing the target-cells;

c. incubating the mixture under gentle rotation;

d. examining the target-cells after incubation; and e. counting the target-cells after incubation.

2. The method of claim 1, wherein the paramagnetic particle or bead is coated with a murine or a human antibody or fragment thereof.

3. The method of claim 1, wherein incubating lasts for 5-10 minutes to 2 hours.

4. The method of claim 3, wherein incubating lasts 30 minutes.

5. The method of claim 1, wherein incubating is at a temperature between 0° C. and 25° C.

6. The method of claim 5, wherein incubating is at a temperature of about 4° C.

7. The method of claim 1, wherein when the target cell population is contained in blood or bone marrow aspirates, the method, further comprises the step of:

pre-incubating the antibody-coated paramagnetic particle and the cell suspension with mild detergent.

8. The method of claim 7, wherein the preincubating comprises as detergent Tween 20™ (polyoxyethylenesorbitan monolaurate) at a concentration less than 0.1% and the preincubation lasts 30 minutes at 4° C.

9. The method of claim 1, wherein when the density of target-cells is low, or when the ratio of target cell/total cells in the cell mixture is low (≦1%), the method further comprises the step of:

subjecting the incubated paramagnetic particle-antibody-cell mixture to a magnetic field.

10. The method of claim 9, wherein the particle-target-cell complexes are stained.

11. The method of claim 1, wherein the step of examining, the step of counting, or both steps comprise using a microscope or a cell or particle counting device.

12. The method of claim 1, further comprising the steps of:

isolating the target-cells by exposing the complex of cells and paramagnetic particles to a magnetic field to magnetically aggregate the cells;

subjecting the magnetically aggregated cells to further biological, biochemical, and immunological examination.

13. The method of claim 1, wherein the antibody or fragment thereof is directed against an antigen or a receptor in a cell with abnormal developmental patterns.

14. The method of claim 13, wherein the cell is a primary or a metastatic cancer cell.

15. The method of claim 13, wherein the antibody or antibody fragment is directed against breast, ovarian or lung carcinoma cells; melanoma, sarcoma, glioblastoma or cancer cells of the gastrointestinal tract; melanoma, sarcoma, glioblastoma or cancer cells of the genitourinary tract; or melanoma, sarcoma, glioblastoma or cancer cells of the reticuloendothelial system.

16. The method of claim 1, wherein the antibody or fragment is of IgG isotype, a $F(ab')_2$ fragment, a F(ab) fragment, IgM, or a fragment of IgM.

17. The method of claim 1, wherein the cell suspension or population comprises mammalian tissue, a pleural effusion, a peritoneal effusion, a body fluid, or a solid tumor in a normal tissue or organ.

18. The method of claim 17, wherein the mammalian tissue comprises human bone marrow or human peripheral blood; the body fluid comprises urine, cerebrospinal fluid, semen, or lymph; or the normal tissue or organ comprises liver, lymph node, spleen, lung, pancreas, bone, central nervous system, prostate gland, skin, or mucous membranes.

19. A kit for performing the method of claim 1, the kit comprising:

a. a specific antibody or antibody fragment directed to an antigen on a target-cell, which antibody or fragment is effective for coating a paramagnetic particle or bead without removing its antigen-binding ability;

b. a paramagnetic particle or bead; and c. another specific antibody or antibody fragment directed against an antigen or a receptor within or on the target cell;

wherein said another antibody or antibody fragment is conjugated to biotin or to an enzyme; or wherein said another antibody or antibody fragment is bound to a non-paramagnetic particle with a specific color or with a bound enzyme.

20. The kit of claim 19, wherein the enzyme is peroxidase or alkaline phosphatase.

21. A method for detecting a specific living target cell in a cell suspension of a mixed cell population at a sensitivity of one target cell per 100 or more total cells, in a fluid system containing a mixed cell population, or in a single cell suspension prepared from a solid tissue, with the exception of normal and malignant hematopoietic cells in blood and bone marrow, the method comprising the steps of:

a. coating paramagnetic particles or beads with an antibody or antibody fragment directed against a membrane structure specifically expressed on the target-cell and not on a non-target-cell in the cell mixture;

b. mixing the coated paramagnetic particles or beads with the cell suspension containing the target-cells;

c. incubating the mixture under gentle rotation; and d. examining the target-cells after incubation.

*22. A method for detecting and quantitating a specific living target cell in a cell suspension of mixed cell population at a sensitivity of one target-cell per 100 or more total cells, in a fluid system containing a mixed cell population, or in a single-cell suspension prepared from a solid tissue, the method comprising the steps of:*

*(a) coating paramagnetic particles or beads with an antibody or antibody fragment directed against a membrane structure specifically expressed on the target cell and not on a non-target-cell in the cell mixture;*

*(b) mixing the coated paramagnetic particles or beads with the cell suspension containing the target-cells;*

*(c) pre-incubating the antibody-coated paramagnetic particle and the cell suspension with mild detergent;*

*(d) incubating the mixture under gentle rotation;*

*(e) examining the target-cells after incubation; and*

*(f) counting the target-cells after incubation.*

*23. The method of claim 22, wherein the paramagnetic particle or bead is coated with a murine or a human antibody or fragment thereof.*

*24. The method of claim 22, wherein incubating lasts for 5-10 minutes to 2 hours.*

*25. The method of claim 24, wherein incubating lasts 30 minutes.*

*26. The method of claim 22, wherein incubating is at a temperature between 0° C. and 25° C.*

*27. The method of claim 26, wherein incubating is at a temperature of about 4° C.*

*28. The method of claim 22, wherein said mild detergent comprises polyoxyethylenesorbitan monolaurate at a concentration less than 0.1% and the preincubation lasts 30 minutes at 4° C.*

*29. The method of claim 22, wherein when the density of target-cells is low, or when the ratio of target cell/total cells in the cell mixture is low (<1%), the method further comprises the step of: subjecting the incubated paramagnetic particle-antibody-cell mixture of a magnetic field.*

*30. The method of claim 29, wherein the particle-target-cell complexes are stained.*

*31. The method of claim 22, wherein the step of examining, the step of counting, or both steps comprise using a microscope or a cell or particle counting device.*

*32. The method of claim 22, further comprising the steps of:*

*isolating the target-cells by exposing the complex of cells and paramagnetic particles to a magnetic field to magnetically aggregate the cells;*

*subjecting the magnetically aggregated cells to further biological, biochemical, and immunological examination.*

*33. The method of claim 22, wherein the antibody or fragment thereof is directed against an antigen or a receptor in a cell with abnormal developmental patterns.*

*34. The method of claim 33, wherein the cell is a primary or a metastatic cancer cell.*

*35. The method of claim 33, wherein the antibody or antibody fragment is directed against breast, ovarian or lung carcinoma cells; melanoma, sarcoma, glioblastoma or cancer cells of the gastrointestinal tract; melanoma, sarcoma, glioblastoma or cancer cells of the genitourinary tract; or melanoma, sarcoma, glioblastoma or cancer cells of the reticuloendothelial system.*

*36. The method of claim 22, wherein the antibody or fragment is of IgG isotype, a $F(ab')_2$ fragment, a F(ab) fragment, IgM, or a fragment of IgM.*

*37. The method of claim 22, wherein the cell suspension or population comprises mammalian tissue, a pleural effusion, a peritoneal effusion, a body fluid, or a solid tumor in a normal tissue or organ.*

*38. The method of claim 37, wherein the mammalian tissue comprises human bone marrow or human peripheral blood; the body fluid comprises urine, cerebrospinal fluid, semen, or lymph; or the normal tissue or organ comprises liver, lymph node, spleen, lung, pancreas, bone, central nervous system, prostate gland, skin, or mucous membranes.*

*39. A kit for performing the method of claim 22, the kit comprising:*

(*a*) *a specific antibody or antibody fragment directed to an antigen on a target-cell, which antibody or fragment is effective for coating a paramagnetic particle or bead without removing its antigen-binding ability;*

(*b*) *a paramagnetic particle or bead; and*

(*c*) *another specific antibody or antibody fragment directed against an antigen or a receptor within or on the target cell;*

*wherein said another antibody or antibody fragment is conjugated to biotin or to an enzyme; or wherein said another antibody or antibody fragment is bound to a non-paramagnetic particle with a specific color or with a bound enzyme.*

*40. The kit of claim 39, wherein the enzyme is peroxidase or alkaline phosphatase.*

*41. A method for detecting a specific living target cell in a cell suspension of a mixed cell population at a sensitivity of one target cell per 100 or more total cells, in a fluid system containing a mixed cell population, or in a single cell suspension prepared from a solid tissue, the method comprising the steps of:*

(*a*) *coating paramagnetic particles or beads with an antibody or antibody fragment directed against a membrane structure specifically expressed on the target cell and not on a non-target-cell in the cell mixture;*

(*b*) *mixing the coated paramagnetic particles or beads with the cell suspension containing the target-cells;*

(*c*) *pre-incubating the antibody-coated paramagnetic particle and the cell suspension with mild detergent;*

(*d*) *incubating the mixture under gentle rotation; and*

(*e*) *examining the target-cells after incubation.*

* * * * *